United States Patent [19]

Winey

[11] 4,148,987
[45] Apr. 10, 1979

[54] RADIATION-CURABLE MONOMERS AND POLYMERS THEREOF

[75] Inventor: Donald A. Winey, Warminster, Pa.

[73] Assignee: Rohm and Haas Company, Philadelphia, Pa.

[21] Appl. No.: 793,656

[22] Filed: May 4, 1977

[51] Int. Cl.² .................................. C07C 69/76
[52] U.S. Cl. .............................. 526/316; 260/29.6 R;
260/29.6 H; 260/29.6 T; 260/29.6 TA;
260/567.6 M; 260/570 AB; 260/590 D;
260/591; 260/592; 560/51; 560/52; 427/43;
427/54; 427/207 B; 427/385 R; 427/390 R;
427/391; 427/393; 428/288; 428/290;
204/159.14
[58] Field of Search ............... 560/51, 52; 562/316;
260/29.6 R, 29.6 T, 29.6 H, 29.6 TA

[56] References Cited

U.S. PATENT DOCUMENTS

| | | | |
|---|---|---|---|
| 2,213,783 | 9/1940 | Kyrides | 560/52 |
| 3,429,852 | 2/1969 | Skoultchi | 260/47 |
| 3,574,617 | 4/1971 | Skoultchi | 96/35.1 |
| 4,058,558 | 11/1977 | Cousse et al. | 560/51 |

FOREIGN PATENT DOCUMENTS 463011  2/1950 Canada ........................... 560/52

Primary Examiner—Jane S. Myers
Attorney, Agent, or Firm—Carl A. Castellan; Lester E. Johnson

[57] ABSTRACT

Monoethylenically unsaturated derivatives of substituted benzophenones or acetophenones which are prepared by reaction of such a benzophenone or acetophenone with a vinyl benzyl halide, such as the chloride, are polymerizable to form homopolymers or copolymers e.g. with a wide variety of conventional ethylenically unsaturated monomers, especially monoethylenically unsaturated vinyl or vinylidene monomers. The resulting polymers are sensitive to radiation, such as ultraviolet light, e.g. having a wave length of 2,000 to 5,000 angstroms, and readily cross-link or cure upon exposure to such radiation. Adhesives, binders, coatings, and impregnating compositions are made from the polymers.

10 Claims, No Drawings

RADIATION-CURABLE MONOMERS AND POLYMERS THEREOF

BACKGROUND OF THE INVENTION

Polymers of monoethylenically unsaturated vinyl monomers have many uses because of their outstanding physical properties and their adaptability to economical manufacture. However, they have disadvantages which tend to limit their usefulness, such as susceptibility to action of solvents, lack of resistance to gasoline, oil, and grease, excessive flexibility and lack of resilience, and loss of dimensional stability and strength at relatively low temperature.

Various crosslinking techniques have been resorted to in trying to overcome the disadvantages mentioned that are associated with the conventional linear, two-dimensional form. Such techniques have generally not been completely practical because they sometimes necessitate the use of harsh reaction conditions and often result in degradation of the polymer, instability thereof to heat, and serious susceptibility to heat. The use of extraneous photosensitizers blended with the polymers encounter problems of compatibility, uniformity of distribution, volatility, toxicity, or exudation and migration of the additive, often resulting in premature and/or erratic crosslinking. It has been suggested in Tocker, U.S. Pat. No. 3,214,492 and Skoultchi, U.S. Pat. No. 3,429,852 to provide certain acetophenone or benzophenone derivatives having acryloxy or methacryloxy groups so that such compounds can be copolymerized with ethylene or with other vinyl monomers to provide copolymers that can be cured (i.e. crosslinked) after shaping by exposure to radiation. In general, however, these monomeric compounds are relatively expensive to manufacture.

SUMMARY OF THE INVENTION

In accordance with the present invention, a new class of photomonomers is provided that have the advantages of easy preparation, frequently from convenient, relatively inexpensive, commercial raw materials, and of good reactivity of the vinyl (i.e. monomeric) and the photoactive portions of the molecule. In general, the vinyl portion is a simple vinyl group substituted in the phenyl nucleus of a benzyl group and the photoactive portion is an acetophenone or benzophenone group which may be substituted. The two portions may be linked by an ether atom (—O—), an ester linkage

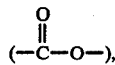

or an amine nitrogen atom

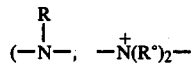

wherein R is H or alkyl having 1 to 8 carbon atoms, and R° is alkyl having 1 to 4 carbons, R preferably being H or methyl and R° preferably being methyl). The novel photomonomers of the present invention are those of one of the following formulas:

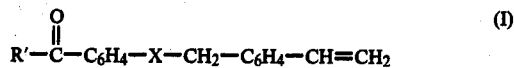

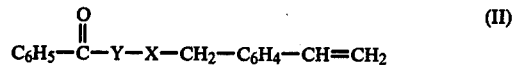

wherein
R' is a phenyl group or an alkyl group having 1 to 3 carbon atoms,
Y is a saturated or unsaturated aliphatic group (a) of straight or branched chain type having 1 to 3 carbon atoms, or (b) of cyclic type having 3 to 6 carbon atoms, and
X is —O—, —C(O)O—, —N(R)—, and —N+(R°)$_2$—, R being H or alkyl having 1 to 8 carbon atoms, and R° being an alkyl group having 1 to 4 carbon atoms.
R' is preferably phenyl or methyl, X is preferably —C(O)O—, and Y is preferably an ethylene group.

In formulas I and II given above, the group —C$_6$H$_4$— represents the divalent phenylene group to which the two substituents may be bonded in ortho, meta, or para relationship. In formula II, the C$_6$H$_5$—group represents the phenyl radical. Formulas I and II can be more definitely represented in general form as follows:

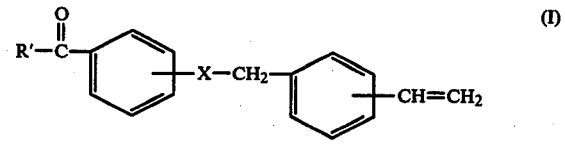

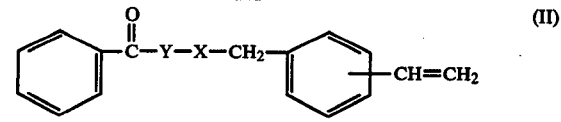

wherein R', X, and Y have the same definitions as stated above.

These monomers (hereinafter sometimes referred to as "phenone" monomers) can be made and generally are made, from a vinyl benzyl halide, such as the chloride, by reaction thereof with a suitable acetophenone or benzophenone derivative, the choice of which depending upon the particular photoactive monomer desired, i.e. the particular R' and X groups desired and the particular Y group, if present in the monomer. For example, the use of o-benzoylbenzoic acid yields a product of formula I in which R' is phenyl and X is —C(O)O—.

Other acetophenone and benzophenone derivatives which can be reacted with vinylbenzyl chloride to give the desired photoactive monomer include:

| Material | Structure Formula | R' | Y | X |
|---|---|---|---|---|
| acetylbenzoic acid, (o,m,p) | I | CH$_3$ | — | C(O)O |
| benzoylbenzoic acid, (o,m,p) | I | φ | — | C(O)O |
| hydroxybenzophenone, (o,m,p) | I | φ | — | O |
| hydroxyacetophenone, (o,m,p) | I | CH$_3$ | — | O |
| aminoacetophenone, (o,m,p) | I | CH$_3$ | — | NH |

| | | Structure | | |
|---|---|---|---|---|
| Material | Formula | R' | Y | X |
| dimethylaminobenzophenone, (o,m,p) | I | φ | — | N+(Me)₂ |
| 3-(benzoyl)-propionic acid | II | — | —CH₂CH₂— | C(O)O |
| beta-(benzoyl)-acrylic acid | II | — | —CH=CH— | C(O)O |
| 4-(benzoyl)-butyric acid | II | — | —C₃H₆— | C(O)O |

Footnote:
φ represents phenyl

The monomer of formula I of the present invention may be prepared by reacting the vinyl benzyl halide, preferably the chloride, which may consist of any one of the position isomers, ortho, meta, or para, or a mixture of two or three such isomers, with an acetophenone or benzophenone derivative (phenone derivative) containing, in an aryl, i.e. phenyl, ring, a group that has a hydrogen atom reactive with the halide atom to eliminate the resulting hydrogen halide or a tertiary amino group that is quaternized by reaction with the vinyl benzyl halide. The reaction may be carried out in any suitable inert solvent for both reactants, e.g. dimethyl formamide, dimethyl acetamide, acetonitrile, tetrahydrofurane, dimethyl sulfoxide, or the like. The temperature may range from room temperature or below, e.g. 10° C. to 25° C. up to 150° C. or higher, preferably between 40° C. and 100° C. In using a carboxyl derivative, it may be converted to a salt, e.g. of an alkali metal, by means of caustic soda or potash or the carbonates thereof, before or concurrently with the reaction with the vinyl benzyl halide. Similarly, when the reactive group in the phenone derivative is a hydroxyl group, the latter may be converted to an alkali metal alcoholate by the addition of caustic soda or potash or the analogous alkali metal carbonates. When the reactive group is a primary or secondary amine group, there is included in the reaction medium, a hydrogen halide accepting agent, e.g. a tertiary amine or an inorganic alkaline material, such as caustic soda or potash. At the completion of the reaction, the monomer product may be recovered from the reaction medium such as by filtration to remove salts formed, and distillation of solvent when used.

When the phenone derivative contains a tertiary amine group, the vinyl benzyl halide "alkylates" or quaternizes the tertiary amine group, the mixture being heated while undergoing agitation in an aqueous or aqueous-alcoholic medium to favor ionization and thereby dispersion of the quaternary monomer formed.

The monomers of formula II may similarly be prepared from benzoyl-substituted aliphatic compounds containing an analogous reactive group in the aliphatic component of the starting reactant.

Generally, the monomer products of formulas I or II may include mixtures of position isomers depending upon the nature of the starting materials, i.e. whether they consist of a single position isomer or a mixture of two or more thereof. Both types of monomers are essentially equivalent in utility.

In general, the reaction to prepare the monomers of formulas I and II is carried out, with or without an inert solvent, i.e. one that is not reactive under the conditions involved herein, while agitating the mixture, the vinyl benzyl halide being added to the other reactant containing a suitable catalyst if desired, such addition being in large amounts rapidly or gradually and being accompanied by heating, or cooling if the reaction is exothermic.

In general, the preparation of the monomers of this invention may be conducted at any temperature which will be high enough so as to result in an adequate reaction rate. In addition, the length of the reaction period will depend, for the most part, upon the specific phenone derivative or benzoyl reagent utilized. Thus, it is a matter of ordinary preparative experience on the part of the practitioner to determine the precise combination of time and temperature which will be best suited for his synthesis of any of the novel phenone derivatives coming within the scope of this invention, since the examples herein are merely illustrative.

Upon the completion of the reaction and with subsequent cooling of the reaction vessel to room temperature, the resulting products will ordinarily be in the form of viscous oils. For most purposes, including any subsequent polymerization reaction, this crude ethylenically unsaturated phenone derivative can then be used without any further purification being necessary. However, where desired, the relatively small amount of unreacted benzoyl or phenone intermediate may be removed. Thus, such means as chromatographic separation techniques, for example a silica gel column can be used. Other separation techniques, such as aqueous alkali or organic solvent extraction procedures, may also be used where so desired by the practitioner. Thus, when a solvent is used in preparing the monomer, it would then be recovered by distilling off the solvent whereupon the crude product could, again, be purified by means of the above noted techniques.

In utilizing the monomers of the present invention in the preparation of homo- and copolymers, there may be employed any of the usual vinyl polymerization methods which are well known to those skilled in the art and which is particularly suited for the homo- and copolymer whose preparation is desired. Thus, such polymers may be prepared by means of free radical initiated processes utilizing bulk, suspension, solution, or emulsion polymerization techniques; or, they may be prepared by ionic catalysis or by means of stereospecific catalysts such as those of the type developed by Ziegler. The linear polymers may have molecular weights in the range of 10,000 to 300,000 (viscosity average) when made by solution technique, or from 100,000 to 900,000 or more when made by emulsion technique. Chain transfer agents may be used to provide lower molecular weights.

The comonomers which may be utilized together with the above described ethylenically unsaturated phenone derivatives for the preparation of the crosslinkable copolymers of this invention can be any ethylenically unsaturated monomer such, for example, as styrene; alphamethyl styrene; the acrylic and methacrylic acid esters of aliphatic alcohols such as methyl, ethyl, propyl, butyl, isobutyl, amyl, hexyl, 2-ethyl hexyl, octyl, lauryl and stearyl alcohols; acrylic acid, methacrylic acid; isoprene; acrylamide; methacrylamide, acrylonitrile; methacrylonitrile, butadiene; vinyl propionate; dibutyl fumarate; dibutyl maleate; diallyl phthalate; vinylidene chloride; vinyl chloride; vinyl fluoride; vinyl acetate; ethylene; and propylene etc. Any of these monomers may be used either alone or in combination with one another together with one or more of the acetophenone or benzophenone-containing monomers. Preferably, the comonomer(s), used are monoethylenically unsaturated monomers having a single group of the formula $H_2C=C<$.

In order to effectively crosslink upon exposure to ultraviolet light, the copolymers of this invention should contain from about 0.1 to 50% preferably 0.1 to 5%, by weight of at least one of these ethylenically unsaturated phenone monomers of formula I or II. When the concentration of ethylenically unsaturated phenone monomer substantially exceeds about 50% by weight, the crosslinking efficiency of the copolymer is markedly reduced because of the reduced concentration, in the copolymer, of the moieties derived from the conventional monomers.

The copolymers of this invention, whether prepared by means of bulk, suspension, solution, or emulsion polymerization techniques or by other means, are all characterized by their sensitivity to ultra-violet light and thus are readily crosslinked by exposure thereto. This improved crosslinking ability is at least fully equivalent, and in most cases superior, to the results obtained when extraneous photosensitizers are added to the comparable polymers which do not contain these phenone monomers. Moreover, all of the deficiencies which are inherent in the use of these extraneous photosensitizers are completely avoided with the products of this invention. Thus, these novel polymeric compositions exhibit excellent crosslinking ability without the difficulties posed by such problems as volatility, toxicity, migration and premature crosslinking.

In addition to the preparation of conventional copolymers which are prepared by the polymerization of one or more of the novel phenone derivatives of this invention together with one or more vinyl comonomers, it is also possible to prepare graft copolymers wherein the phenone monomer of this invention is polymerized in the presence of previously prepared vinyl polymers such as polyolefins, polyvinyl halides and polyvinyl esters. The resulting graft copolymers also exhibit excellent crosslinking ability upon being exposed to ultra-violet light.

In order to crosslink the novel copolymers of this invention, it is merely necessary to expose them to ultraviolet light, i.e. to radiation having a wavelength about 2,000 to 5,000 Å., for a period of time which is sufficient to accomplish the desired amount of crosslinking and yet which will not result in any undesirable degradation of the copolymer, said degradation being in the form of oxidation and chain cleavage of the copolymer and being manifested by discoloration and a marked deterioration in the physical properties of the copolymer composition. The length of exposure will also be dependent on the source of radiation as well as on the distance between the source and the copolymer sample.

The crosslinking procedure may be conducted while the copolymer is still in the initial physical form resulting from the polymerization procedure. However, it is preferred and more convenient to effect the crosslinking reaction after the polymer has been formed into a shaped article, e.g. a film, coating, or molded article. In either instance, the degree of crosslinking will be determined by the extent to which the copolymer has been insolubilized. Thus, for example, if the copolymer is still in solution, crosslinking will be evidenced by the progressive precipitation or gelation of the dissolved copolymer. On the other hand, if the copolymer has been formed into a shaped article, crosslinking will be noted by the resistance exhibited by the shaped article to solvents in which it would ordinarily dissolve or soften.

The resulting crosslinked compositions can now be used for a wide variety of applications. Thus, they may be used in applications wherein high oil, grease and solvent resistance as well as increased stiffness are required. Specifically, they may be used in photo-reproduction processes, in processes wherein it is desirable to engrave or carve intricate shapes and/or designs without the use of cutting tools, and in industrial construction, etc.

The addition homopolymers and copolymers of the phenone monomers of formula I or II that are of linear, essentially uncrosslinked character retain their formability by virtue of their thermoplastic and soluble nature, so that they can readily be shaped into films, sheets, and other articles and then can be exposed to active radiation, such as ultraviolet light of wave length mentioned hereinabove, to crosslink the polymers and thereby render them infusible and insoluble. For example, the uncrosslinked copolymers may be used as film-forming binders or adhesives in the production of various coating and/or impregnating compositions, such as pigment-dyeing and printing compositions for application to papers and textiles which after application can be rendered resistant to removal by heating or solvents by subjecting the films carried by or in the textiles or papers to actinic radiation. The linear addition copolymers can be used as binders for non-woven fabrics or webs. They may be applied uniformly over the entire area of the non-woven web or in any predetermined pattern, e.g. along intersecting sets of parallel lines, either straight or curved in a regular or even somewhat irregular array. The impregnated non-woven web may then be subjected to actinic radiation, e.g. UV light, to crosslink the polymer wherever it is present, thereby rendering the treated non-woven web more or less resistant to disintegration by water or solvents. Instead of applying the linear copolymer of the present invention in a pattern to the non-woven web, it may be applied uniformly throughout the area of the web and then the web may be subjected to the actinic radiation, e.g. ultraviolet light, in a predetermined pattern through a light filter or opaque screen so that selected areas of the polymer film coating or impregnant are protected from the actinic radiation whereas other areas exposed and rendered more or less resistant to solvents and/or water. After the screened exposure, the unexposed portions of the polymer may be removed by washing, as by an aqueous or organic solvent.

The copolymers of the present invention may be used to produce "wet wipes", disposable diapers and/or diaper covercloths. The use of a screen or filter can control the extent of crosslinking selectively in various areas of the bonded diaper or diaper covercloth so that, for example, the crotch area can be rendered resistant to disintegration by water-soaking whereas the peripheral areas can be disintegrated within a short time of half a minute to two minutes or so on soaking in water. The crotch area may be of sufficiently small size that it will not interfere with the flushing of the entire diaper and/or diaper covercloth down the toilet after use.

In the following examples which are illustrative of the invention, the parts and percentages are by weight and the temperatures are Centigrade unless otherwise expressly noted.

EXAMPLE 1

Preparation of

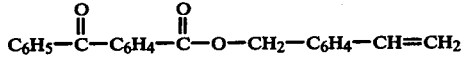

To a flask equipped with an efficient stirrer, thermometer, addition funnel and a reflux condenser there are charged dimethyl formamide 200 g, sodium carbonate (solid powder) 0.55 mole, 58.3 g and vinylbenzyl chloride (VBC) (commercial material, mixture of m and p isomers) 0.55 mole, 83.6 g. This slurry is stirred and heated to 100° C. where the temperature is automatically controlled. While stirring and maintaining 100° C. 200 g of a solution of 113 g of o-benzoylbenzoic acid (0.50 mole) in dimethyl formamide is added evenly over 60 min. Thirty minutes after the feed is complete, GLC shows that the VBC has almost completely reacted: IR spectra confirm that the keto-ester product is formed. The solution of product is separated from the solids by filtration and is stripped free of solvent on a rotary evaporator. The product (vinylbenzyl o-benzoylbenzoate) is a fluid amber oil (sometimes designated hereinafter as VBBB), 178 g recovered, about 95% pure, over 95% yield.

EXAMPLE 2

Preparation of

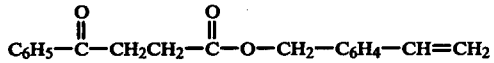

To a flask equipped with an efficient stirrer, a thermometer, an addition funnel and a reflux condenser there are charged 40.0 g of about 50% aqueous NaOH solution, (500 meq) and 24 g of deionized water. To this solution is added 3-benzoylpropionic acid (500 meq, 89.1 g). The formation of the salt is exothermic with the temperature reaching 52° C. At this point the pH is 12.5 and 2×5 g shots of 3-benzoylpropionic acid are required to reach a pH of 7.5. The solution has a titer of 3.24 meq/g; 527.8 meq of salt for reaction.

The salt solution is maintained at 55–60° C. and vinylbenzyl chloride (498 meq, 75.9 g), t-butyl pyrocatechol (0.05 g) and benzyltriethylammonium chloride (25 meq, 5.9 g) are charged. With vigorous stirring of the two-phase system, temperature is increased to 90° C. and held there until reaction is greater than 90% as determined by disappearance of the carboxylic acid salt (8 hr. required).

The reaction is cooled to about 75° C. and then there are charged 80 g H2O containing 5.5 g of Na2CO3 and styrene (120 g). After mixing thoroughly stirring is stopped and the aqueous phase is removed (190 g removed). The organic phase is azeotroped dry (to 80° C. in pot at 75 mm Hg), cooled, filter aid added, and filtered to yield 231 g of solution. By saponification the solution is found to be 48.6% keto-ester product for a yield of 76.5%. This product, vinylbenzyl 3-benzoylpropionate is hereinafter sometimes designated VBBP.

EXAMPLE 3

Preparation of

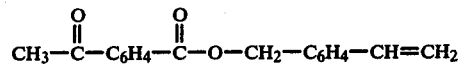

The procedure of Example 1 is repeated except that instead of o-benzoylbenzoic acid, there is used 82.0 g of p-acetylbenzoic acid. The keto-ester product is obtained in a yield of about 85%.

EXAMPLE 4

Preparation of

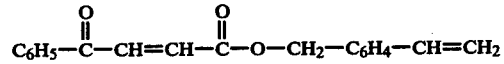

The procedure of Example 2 is repeated except that beta-(benzoyl)-acrylic acid (88 g) is substituted for the 3-(benzoyl)-pyropionic acid. The keto-ester product is recovered in a yield of about 73%.

EXAMPLE 5

Preparation of

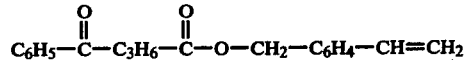

The monomer product of this structure is obtained in essentially the same way as the monomer of Example 2 except that 96.0 g of 4-(benzoyl)-butyric acid is used instead of 3-(benzoyl)-propionic acid. The keto-ester of the formula in the title of this example is recovered in about 70% yield.

EXAMPLE 6

Preparation of 

Into a reaction vessel equipped with a stirrer, thermometer, a feeding-funnel, a reflux condenser and a jacket for heating or cooling, there are charged 200 g dimethyl formamide, 58.3 g (0.55 mole) of powdered Na2CO3 and 83.6 g (0.55 mole) of vinylbenzyl chloride (VBC) (a commercial mixture of meta and para isomers); this mixture is heated while agitating till it reaches 95° C. where it is maintained while 200 g of a solution of 100 g (0.5 mole +) of p-hydroxy benzophenone in dimethyl formamide is added gradually over a period of about an hour. Stirring is continued for another hour at which time GLC shows that the reaction of the VBC is practically complete and the keto-ether product is filtered to remove solids and stripped of solvent, e.g. on a rotary evaporator. The oily liquid product is recovered in about 90% purity and at a yield of about 93%. IR spectra confirms the ketoether structure of the product.

EXAMPLE 7

Preparation of 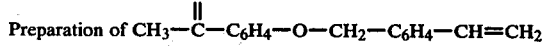

This keto-ether product is obtained by repeating essentially the same procedure of Example 6 except that the solution in dimethyl formamide of p-hydroxybenzophenone is replaced by 200 g of a solution of 68.0 g of hydroxyacetophenone (mixture of ortho and para isomers).

EXAMPLE 8

Preparation of 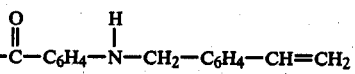

To produce this keto-amine product, the reaction vessel is charged with 200 g of dimethyl formamide, 83.6 g of VBC, and 58.3 g powdered sodium carbonate as in Example 1 and this mixture is heated to 100° C. with stirring. Then while maintaining the temperature at this level, there is gradually added 200 g of a solution in dimethyl formamide containing 68 g of p-aminoacetophenone over a period of about an hour. The mixture is then held at this temperature for another 30 minutes to assure completion of the reaction of the VBC. The oily liquid product is recovered in a yield of 95% after filtration and stripping off the solvent.

EXAMPLE 9

Preparation of

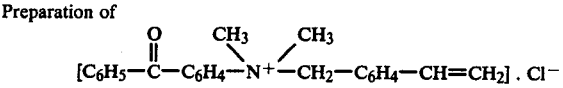

A solution of 92.5 g of o-(dimethylamino)-benzophenone in 100 g of dimethyl formamide is placed in a glass reaction vessel and heated to 6° C. Then a solution (200 g total weight) in dimethyl formamide of 83.6 g of vinylbenzyl chloride is added gradually over a period of about half an hour. After completion of the addition, the solvent is distilled, leaving the keto-quaternized amino product with a yield of 97% to 99%.

Illustrative Examples of Addition Polymers

EXAMPLE 10

(a) A homopolymer is prepared from the monomer of Example 1 by dissolving 20 g of that monomer in dimethyl formamide and heating the resulting solution in a glass reaction vessel to a temperature of 100° C. whereupon 0.2 g of t-butyl peroctoate is added. As the temperature declines to 100° C. after an initial rise thereof, more monomer and more peroctoate initiator are gradually added in the same relative proportions. The homopolymer may be used in the form of a solution to deposit a protective film on substrates of metal, wood, and paper which on exposure to UV light become crosslinked in solvent-resistant form.

(b) Homopolymers are prepared from the monomers obtained in each of the other examples 2 through 9. They also can be applied to substrates in the same way and then crosslinked by exposure to UV radiation.

EXAMPLE 11

A monomer solution (A) of butyl acrylate (BA), 477.5 g; acrylic acid (AA) 15 g; monomer obtained in Example 1 (VBBB), 7.5 g, and 2-hydroxyethylmercaptan (2-HEM), 0.5 g is prepared. To a flask equipped with a stirrer, thermometer, addition funnel, nitrogen inlet, and reflux condenser is charged toluene, 65 g and 30 g of the monomer solution A. A solution (B) of t-butyl-peroctoate, 1.0 g in 25 g of toluene is also prepared. The flask charge is heated to 100° C. whereupon 1.6 g of solution B is added and heating is then continued to reflux (111° C.). The remaining A and B are combined and added to the flask over a 3 hr. period beginning 15 minutes after the initial charge of B. As the polymerization proceeds the pot temperature increases and is limited to 115° C. by an automatic temperature control. Thirty minutes after the monomer feed is complete a chaser catalyst charge of t-butylperoctoate, 0.5 g in toluene, 3.0 g, is added and 115° C. is maintained for 60 additional minutes. The polymer at this point is a viscous fluid having 82.4% solids, conversion calculated 97.6%. The bulk of the toluene is removed by applying vacuum while heating at 100°–110° C. This produces a slightly hazy, pale yellow highly viscous resin. Solids 96.4%, viscosity 1,660,000 cps (#4 at 0.3 rpm and 25° C.).

EXAMPLE 12

Proceeding as in Example 11 but using 470 g of butyl acrylate and 15 g of VBBB a similar polymer having 91.5% solids and 460,000 cps (#4 at 0.6 rpm and 25° C.) is prepared.

EXAMPLES 13–19

| Example | BA | AA | VBBB | 2-HEM | Solids (%) | Viscosity (cps) |
|---|---|---|---|---|---|---|
| 13 | 490 | 5 | 5 | 1.25 | 96.8 | 198,000 (#4 at 3) |
| 14 | 490 | 5 | 5 | 2.50 | 97.0 | 102,000 (#4 at 3) |
| 15 | 490 | 5 | 5 | 5.00 | 99.0 | 58,000 (#4 at 6) |
| 16 | 490 | 5 | 5 | 7.50 | 98.5 | 28,000 (#4 at 6) |
| 17 | 492.5 | 5 | 2.5 | 1.25 | 99.8 | 372,000 (#4 at 1.5) |
| 18 | 493.75 | 5 | 1.25 | 1.25 | 98.2 | 304,000 (#4 at 1.5) |
| 19 | 494.5 | 5 | 0.50 | 1.25 | 99.2 | 440,000 (#4 at 0.6) |

EXAMPLES 20–22

Proceeding as in Example 11 the following polymers are prepared:

| Example | BA | AA | AN | VBBB | 2-HEM | Solids (%) | Viscosity (cps) |
|---|---|---|---|---|---|---|---|
| 20 | 96 | 3 | 0 | 1.0 | 0.10 | 83.8 | 39,000 (#4 at 6) |
| 21 | 95.5 | 3 | 0 | 1.5 | 0.10 | 85.6 | 40,000 (#4 at 6) |
| 22 | 94 | 2.5 | 2.5 | 1.0 | 0.10 | 84.4 | 50,000 (#4 at 6) |

EXAMPLE 23

To a flask equipped with a stirrer, thermometer, addition funnels and nitrogen inlet is charged deionized (DI) water 521 g, Triton X-405 (70% active ingredient, t-octylphenoxypoly (39)ethoxyethanol) 25.7 g, 36 g of a 0.1% aqueous solution of FeSO$_4$.7 H$_2$O, 9.9 g of a 1% aqueous solution of Versene, acetic acid 0.10 g, ethyl acrylate 177.3 g, VBBB monomer of Example 1 above, 2.7 g and 2-hydroxyethylmercaptan (mercaptoethanol) 0.90g. This seed charge is sparged with nitrogen for 60 minutes while the following solutions and emulsion are prepared.

| Solution 1 | sodium formaldehyde sulfoxylate 0.36 g |
| | DI water 22 g |
| Solution 2 | sodium hydrosulfite 0.95 g |
| | DI water 5 g |
| Solution 3 | Triton X-405 25.7 g |
| | DI water 34 g |
| Solution 4 | sodium formaldehyde sulfoxylate 1.44 g |
| | DI water 110 g |
| Emulsion | DI water 306.0 g |
| | Triton X-405 25.7 g |
| | 2-hydroxyethylmercaptan 3.6 g |
| | Monomer of Example 1 (VBBB) 10.8 g |
| | ethyl acrylate (EA) 709.2 g |
| | diisopropylbenzene hydroperoxide (DIBHP) (55% active) 5.2 g |

After 60 minutes of nitrogen sparge the nitrogen stream is removed from the liquid but is continued as a sweep through the system. The polymerization is initiated by adding diisopropylbenzene hydroperoxide (55% active) 1.3 g followed by Solutions 1 and 2. The exothermic polymerization begins in less than 5 minutes and raises the temperature from about 25° C. to about 60° C. in 20 minutes. Five minutes after peak temperature is reached, Solution 3 is added. Four minutes later the 3-hour feeds of Solution 4 and the monomer emulsion are begun. Cooling, as required to maintain 57–60° C., is supplied during the three-hour feeds. After these feeds are completed, the batch is held at 60° C. for fifteen minutes before a last catalyst charge of DIBHP 1.6 g and sodium formaldehyde sulfoxylate 0.45 g in 26 g of DI water is added. Thirty minutes after the last charge is complete and may be cooled and filtered. Properties are: Solids, 45.2%; conversion, 96.6%; wet gum, 0.02%; pH 2.7; viscosity, 120 cps (#3 at 30 rpm); light scatter (0.22% solids) 31.4%.

EXAMPLE 24

Proceeding as in Example 23, a polymer with the composition 97 EA/1.5 VBBP (monomer of Example 2)/1.5 styrene (St) is prepared. Properties are: Solids 44.8%; conversion 95.7%; wet gum 0.10%; pH 2.7; viscosity, 200 cps; light scatter (0.22% solids) 21%.

EXAMPLE 25

An emulsion copolymer of 97 EA/1.5 St/1.5 VBBB (monomer of Example 1) is prepared by the same procedure as that used in Example 23.

EXAMPLE 26

The emulsion copolymers of Example 24 and 25 and an emulsion polymer of 100% EA prepared by a procedure essentially the same as those used to produce the aqueous polymer dispersions obtained in Examples 24 and 25 are applied to a creped paper weighing 68 g/m² obtained from the wet-laying of a paper pulp containing a small proportion of long cellulosic fibers in addition to the wood pulp fibers of conventional paper-making length. Herein, the EA homopolymer is a control and is designated Polymer A, the copolymer of Example 25 is designated Polymer B and the copolymer of Example 24 is designated Polymer C.

The three polymer dispersions are diluted to 3% solids concentration. Separate sheets of the paper are placed between glass fiber screens to support the paper as it is passed through a respective one of the 3% solids polymer dispersions and then through the squeeze rolls of a textile padder adjusted to provide a dry add-on (after drying the treated paper at 60° C. for 15 minutes) of 4 to 6%. Half of each treated paper after drying at 60° C. for 15 minutes is passed twice (one pass for each side) on a conveyor belt through an ultraviolet curing range consisting of two 80 W/cm mercury vapor lamps in a housing through which the paper is conveyed at a speed of 4.5 m/sec.

Strips of treated paper were soaked in water for 30 min. and tensile tested in the cross machine direction using the cut-strip method described in ASTM D1117-69 (7.6 cm gage length, 30.5 cm/min). Results are shown in Table I. Although UV exposure increased strength in the absence of photomonomer (Copolymer A) due to degradative crosslinking of EA, significantly higher cured strengths and higher ratios of cured to uncured strengths are attained with photomonomer present (Copolymers B and C).

TABLE I

| Wet Tensile Strengths of Bonded Papers | | | |
|---|---|---|---|
| | Breaking Force, Newton/Meter | | |
| Binder Copolymer | Uncured | UV Cured | Ratio |
| A | 63 ± 5 | 131 ± 9 | 2.1 |
| B | 78 ± 3 | 415 ± 22 | 5.3 |
| C | 86 ± 5 | 311 ± 26 | 3.6 |

Confidence intervals are 95% limits

EXAMPLE 27

This example illustrates the selective, differential curing of a copolymer of the present invention to provide various degrees of crosslinking in selected areas of a fibrous web such as may be applied in the making of flushable non-woven diaper cover cloth where it is desired to provide high wet strength in the crotch area and relatively lower wet strength in the peripheral area. On disposal in a toilet the bulk of such a diaper cover disintegrates, and the crotch area is small enough to pass through the sanitary plumbing system without clogging it.

A flushable diaper covercloth is made with an air-liad web weighing 60 g/m² and composed of 25% 1.5 denier, 4 cm. rayon fiber and 75% wood fiber. The wood fiber is of the type used in the absorbent padding under the covercloth in conventional disposable diapers. The web is placed between glass fiber screens, passed through a bath containing 5% of the solids of the emulsion polymer obtained in Example 23 and then through the squeeze rolls of a textile padder. The web thus treated is removed from the screens and dried in an oven for 3 minutes at 115° C. The resulting composition of the covercloth is 85% fiber and 15% polymer binder. The bonded web is cut to diaper size, 31 cm by 43 cm, and placed under a cardboard mask. In the center of the mask there is a hole measuring 15 cm by 23 cm with the longer dimension oriented in the longer direction of the covercloth. The mask and covercloth are passed through an ultraviolet curing range to irradiate the center portion of the diaper cover. The cover is then turned over to similarly irradiate the other side.

The UV curing range consists of two 80W/cm mercury vapor lamps and a conveyor belt in a suitable housing. The nonwoven diaper covercloth is run under the lamps at a speed of 4.5 m/sec.

The tensile strength of the cured portion of the web is 120 g/cm of width measured in a soaking wet condition. The uncured portion is moistened to a 60% water content and found to have a tensile strength of 43 g/cm of width.

An entire diaper covercloth treated as above is gently agitated in a bucket full of cold water. The uncured portion of the cloth disintegrates in 1 to 2 minutes leaving the small cured portion intact.

EXAMPLE 28

To 100 parts of the solution polymer produced in Example 12, there is added 20 parts tetrahydrofuran (solvent) to reduce the viscosity. This is coated onto a glass plate at a 3-mil (.0075 cm) thickness, the tetrahydrofuran allowed to evaporate, and the coating exposed to 3 passes under the same 80W/cm, 2-lamp range (described in Example 26 and 27) at 4.5 m/sec. The film of cured polymer is removed from the plate and repeatedly extracted with tetrahydrofuran. It is found to contain 99–100% non-extractables (gel), which proves high crosslink response.

EXAMPLE 29

The solution polymers of Examples 20, 21 and 22, respectively are formulated with 13 parts acetone per 100 parts of polymer to reduce viscosity and are then coated onto 1-mil (0.025 mm) Mylar polyester film, the acetone allowed to evaporate, and the coatings exposed to 2 passes at 4.5 m/sec. through the UV curing range described in Example 27. Coating thickness is 0.038–0.043 mm. The cured films are prepared and tested for their pressure sensitive tape properties according to standard or modified Pressure Sensitive Tape Council Methods. The results and test specifications are tabulated below:

| | Pressure Sensitive Tape Test Results | | Tack | |
|---|---|---|---|---|
| Polymer | 180° Peel Strength[1] (g/cm) | Shear Retention[2] (hr) | Rolling Ball[3] (cm) | Finger Touch[4] |
| Example 20 | 180 | >0.8 | 5.0 | Excellent |
| Example 21 | 180 | >1.5 | 4.8 | Excellent |
| Example 22 | 190 | >0.5 | 7.6 | Excellent |

[1]Pressure Sensitive Tape Council (PSTC) Method No. 1, except the age of the assembly is twenty minutes before testing.
[2]PSTC Method No. 7, except that a ½" overlap is used rather than a 1" overlap.
[3]PSTC Test No. 6
[4]Qualitative panel judgement.

What is claimed is:

1. A monomer selected from the group consisting of those having one of the general formulas:

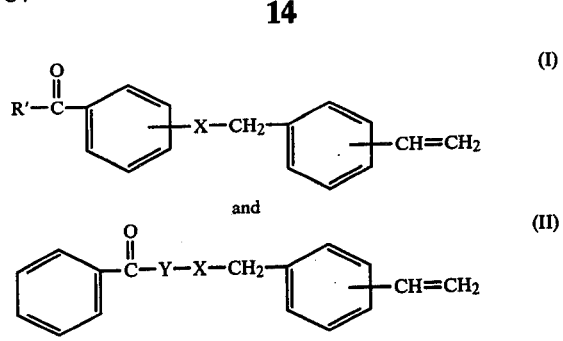

wherein
R' is methyl or phenyl,
X is —C(O)O—, and
Y is a saturated or unsaturated aliphatic group
(a) of straight or branched chain having 1 to 3 carbon atoms, or
(b) of cyclic type having 3 to 6 carbon atoms.

2. A monomer according to claim 1 wherein Y is an ethylene group.

3. Vinylbenzyl benzoylbenzoate.

4. Vinylbenzyl acetylbenzoate.

5. A linear, essentially uncrosslinked addition polymer of a monomer according to claim 1.

6. A cured, crosslinked addition polymer of a monomer according to claim 1.

7. A linear, essentially uncrosslinked addition copolymer of a monomer according to claim 1 with at least one other monoethylenically unsaturated monomer having a group of the formula $H_2C=C<$.

8. A copolymer according to claim 7 having 0.1% to 50% by weight of a monomer according to claim 1 copolymerized therein.

9. A copolymer according to claim 7 having 0.1% to 5% by weight of a monomer according to claim 1 copolymerized therein.

10. A composition for coating and/or impregnating a substrate comprising a solution or dispersion of a copolymer according to claim 9.

* * * * *